United States Patent
Stratakis

(10) Patent No.: US 7,847,078 B2
(45) Date of Patent: Dec. 7, 2010

(54) PDE11A MUTATIONS IN ADRENAL DISEASE

(75) Inventor: Constantine A. Stratakis, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 12/161,866

(22) PCT Filed: Jan. 19, 2007

(86) PCT No.: PCT/US2007/060746

§ 371 (c)(1), (2), (4) Date: Aug. 26, 2008

(87) PCT Pub. No.: WO2007/087493

PCT Pub. Date: Aug. 2, 2007

(65) Prior Publication Data

US 2009/0005337 A1    Jan. 1, 2009

Related U.S. Application Data

(60) Provisional application No. 60/761,446, filed on Jan. 24, 2006.

(51) Int. Cl.
*C07H 21/04* (2006.01)
*C12N 5/00* (2006.01)
*C12N 5/02* (2006.01)
*A61K 48/00* (2006.01)

(52) U.S. Cl. .................... 536/23.2; 435/325; 424/93.21

(58) Field of Classification Search ............... 536/23.2; 424/93.21; 435/325
See application file for complete search history.

(56) References Cited

U.S. PATENT DOCUMENTS

2001/0053519 A1 * 12/2001 Fodor et al. .................... 435/6
2003/0190672 A1 * 10/2003 Omori et al. ................. 435/7.1

FOREIGN PATENT DOCUMENTS

WO  WO 2004/029617 A2  4/2004
WO  WO 2006/092175 A1  9/2006

OTHER PUBLICATIONS

Strategene Catalog, p. 39, 1998.*
Barzon et al., *Eur. J. Endocrinol.*, 149, 273-285 (2003).
D'Andrea et al., *J. Histochem. Cytochem.*, 53 (7), 895-903 (2005).
EBI Accession No. AC073834 (2000).
Fawcett et al., *PNAS*, 97 (7), 3702-3707 (2000).
Gbekor et al., *J. Urol.*, 167 (4), No. 967, 246 (2002).
GenBank Accession No. AB048423.
GenBank Accession No. BAB52712.
GenBank Accession No. BAB62713.
GenBank Accession No. BAB62714.
GenBank Accession No. NM_016953.
GenBank Accession No. NP_058649.
Gunther et al., *J. Clin. Endocrinol. Metab.*, 89 (7), 3173-3182 (2004).
Hetman et al., *PNAS*, 97 (23),12891-12895 (2000).
Horvath et al., *Cancer Res.*, 66 (24), 11571-11575 (2006).
Horvath et al., *Nat. Genet.*, 38 (7), 794-800 (2006).
International Search Report PCT/US2007/060746.
Loughney et al., *Int. J. Impot. Res.*, 17, 320-325 (2005).
Saenz De Tejada et al., *Int. J. Impot. Res., 14 (Suppl 4)*, S20-S32 (2002).
Stratakis, *Horm. Metab. Res.*, 39 (6), 467-473 (2007).
Yuasa et al., *Eur. J. Biochem.*, 268, 168-178 (2001).
Yuasa et al., *Eur. J. Biochem.*, 268, 4440-4448 (2001).
Yuasa et al., *J. Biol. Chem.*, 275 (40), 31469-31479 (2000).

* cited by examiner

*Primary Examiner*—Thaian N Ton
(74) *Attorney, Agent, or Firm*—Leydig, Voit & Mayer, Ltd.

(57) ABSTRACT

The invention provides previously uncharacterized variants of PDE11A that are correlated with a newly discovered form of Cushing Syndrome that presents at a young age. The invention also provides methods useful to research, screen for, treat, or prevent diagnose the disease using the PDE11A variants, as well as other methods relating thereto.

4 Claims, No Drawings

SEQUENCE LISTING

<160> NUMBER OF SEQ ID NOS: 25

<210> SEQ ID NO 1
<211> LENGTH: 461
<212> TYPE: DNA
<213> ORGANISM: Homo sapiens

<400> SEQUENCE: 1

```
tcacgtgtaa acaggcaagg aaagctgtct gggaccatgg cagcctcccg cctggacttt      60
ggggaggtgg aaactttcct ggacaggcac ccagagttgt ttgaagatta cttgatgcgg     120
aagggaagc aggagatggt tgaaaagtgg ctgcagaggc acagtcaggg tcagggggct      180
ttaggtccaa ggccctcttt ggctggacca gcagcttggc tcacagcacc tgcagaggtg     240
gcagcagcgt tggtggtggc actggaccaa atggctctgc ccacagccag cccctttccg    300
gtggcgggga ctgtggtggg gttcccttga gtcccagctg ggccggtggc agcaggggcg     360
atgggaacct gcagcggaga gcttctcaga aagagctaag gaagagtttt gcccgctcca     420
aggccatcca cgtgaacagg acctacgatg aacaggtgac c                          461
```

<210> SEQ ID NO 2
<211> LENGTH: 319
<212> TYPE: DNA
<213> ORGANISM: Homo sapiens

<400> SEQUENCE: 2

```
tctccctgac aacaatgcac atgcagttaa tgctttcttt gtcttatttt taggatcgat      60
gattcaatga tgaaatcgac aagctaactg gatacaagac aaaatcatta ttgtgcatgc     120
ctatccgaag cagtgatggt gagattattg gtgtggccca agcgataaat aagattcctg     180
aaggagctcc atttactgaa gatgatgaaa agtaagatt tcatgccttt tgtgagttgt      240
acttttcttc ttggtcattg attgctattc tcctttaaaa gacaggaatt atgtgaatag     300
ctgttggatt agcccattc                                                  319
```

<210> SEQ ID NO 3
<211> LENGTH: 552
<212> TYPE: DNA
<213> ORGANISM: Homo sapiens

<400> SEQUENCE: 3

```
gagtgtaagt atgtttttaa acatatgaaa tagtttctct acaatgacat taaattcata      60
attttcctc atgtgcagtg tgagctataa agttgttata taacaatagt aattaagaat      120
tttaatgtgc ctatttcccc aaggcctacc tctgtgtaca acaagattgt attttcagac     180
ccatccctgg tggctgcctg ctttcatatt agattttgcc aatgagttgc tgcaatgttt     240
aattagcagg tttgctcttt cctaggcttt tgtcaccttt gtggacttgg catcaacaac    300
acaattatgt atgatcaagt gaagaagtcc tgggccaagc agtctgtggc tcttgatgta     360
agtacagtgt ttatgtcagg tttgtatgct gtcagctcta attttatgag ggaaaaaatt     420
```

-continued

```
tccctggtta tggggcttaa tttctcaaat ttaattattc attgggcctt aatcatttta       480
ggttgtgggt ttaaatctca tgaagtccag agaaacacaa tgttgcatat gatttcaggg       540
gttcacagat gc                                                          552

<210> SEQ ID NO 4
<211> LENGTH: 51
<212> TYPE: DNA
<213> ORGANISM: Homo sapiens

<400> SEQUENCE: 4
tacgattgga acatcaaaaa ccatcatgat atatttcgat caatgttaat g                51

<210> SEQ ID NO 5
<211> LENGTH: 325
<212> TYPE: DNA
<213> ORGANISM: Homo sapiens

<400> SEQUENCE: 5
gccagtttcc attctcctca taagtgaaag gtggaaaatc atgtcagtta ctctgtttcc        60
tctctcctcc acctgtgttt tgttttgttt tgttttaggc actggtgaag gtcaacgtga       120
aactgaagcc gatgctagat tcagtagcta caaacagaag taagtgggaa gagctacacc       180
aaaaacgact gctggcctca actgcctcat cctccctgc cagtgttatg gtagccaagg       240
aagacaggaa ctaaacctcc aggtcagctg cagctgcaaa atgactacag cctgaagggc       300
cattttcagt ccagcaatgt catcc                                            325

<210> SEQ ID NO 6
<211> LENGTH: 20
<212> TYPE: DNA
<213> ORGANISM: Homo sapiens

<400> SEQUENCE: 6
gccagtttcc attctcctca                                                   20

<210> SEQ ID NO 7
<211> LENGTH: 20
<212> TYPE: DNA
<213> ORGANISM: Homo sapiens

<400> SEQUENCE: 7
ggatgacatt gctggactga                                                   20

<210> SEQ ID NO 8
<211> LENGTH: 20
<212> TYPE: DNA
<213> ORGANISM: Homo sapiens

<400> SEQUENCE: 8
tcacgtgtaa acaggcaagg                                                   20

<210> SEQ ID NO 9
<211> LENGTH: 20
<212> TYPE: DNA
<213> ORGANISM: Homo sapiens

<400> SEQUENCE: 9
ggaggtcacc tgttcatcgt                                                   20

<210> SEQ ID NO 10
<211> LENGTH: 20
```

```
<212> TYPE: DNA
<213> ORGANISM: Homo sapiens

<400> SEQUENCE: 10
tctccctgac aacaatgcac                                               20

<210> SEQ ID NO 11
<211> LENGTH: 20
<212> TYPE: DNA
<213> ORGANISM: Homo sapiens

<400> SEQUENCE: 11
gaatgggcta atccaacagc                                               20

<210> SEQ ID NO 12
<211> LENGTH: 20
<212> TYPE: DNA
<213> ORGANISM: Homo sapiens

<400> SEQUENCE: 12
ctatttcccc aaggcctacc                                               20

<210> SEQ ID NO 13
<211> LENGTH: 19
<212> TYPE: DNA
<213> ORGANISM: Homo sapiens

<400> SEQUENCE: 13
gcatctgtga acccctgaa                                                19

<210> SEQ ID NO 14
<211> LENGTH: 21
<212> TYPE: DNA
<213> ORGANISM: Homo sapiens

<400> SEQUENCE: 14
tgtgtttatg tcaccccaca g                                             21

<210> SEQ ID NO 15
<211> LENGTH: 24
<212> TYPE: DNA
<213> ORGANISM: Homo sapiens

<400> SEQUENCE: 15
tcaactgatc tctgaatgtt ttga                                          24

<210> SEQ ID NO 16
<211> LENGTH: 934
<212> TYPE: PRT
<213> ORGANISM: Homo sapiens

<400> SEQUENCE: 16
```

Met Ala Ala Ser Arg Leu Asp Phe Gly Glu Val Glu Thr Phe Leu Asp
1               5                   10                  15

Arg His Pro Glu Leu Phe Glu Asp Tyr Leu Met Arg Lys Gly Lys Gln
                20                  25                  30

Glu Met Val Glu Lys Trp Leu Gln Arg His Ser Gln Gly Gln Gly Ala
            35                  40                  45

Leu Gly Pro Arg Pro Ser Leu Ala Gly Thr Ser Ser Leu Ala His Ser
        50                  55                  60

Thr Cys Arg Gly Gly Ser Ser Val Gly Gly Gly Thr Gly Pro Asn Gly
65                  70                  75                  80

-continued

```
Ser Ala His Ser Gln Pro Leu Pro Gly Gly Gly Asp Cys Gly Gly Val
                85                  90                  95
Pro Leu Ser Pro Ser Trp Ala Gly Gly Ser Arg Gly Asp Gly Asn Leu
            100                 105                 110
Gln Arg Arg Ala Ser Gln Lys Glu Leu Arg Lys Ser Phe Ala Arg Ser
        115                 120                 125
Lys Ala Ile His Val Asn Arg Thr Tyr Asp Glu Gln Val Thr Ser Arg
    130                 135                 140
Ala Gln Glu Pro Leu Ser Ser Val Arg Arg Ala Leu Leu Arg Lys
145                 150                 155                 160
Ala Ser Ser Leu Pro Pro Thr Thr Ala His Ile Leu Ser Ala Leu Leu
                165                 170                 175
Glu Ser Arg Val Asn Leu Pro Gln Tyr Pro Pro Thr Ala Ile Asp Tyr
            180                 185                 190
Lys Cys His Leu Lys Lys His Asn Glu Arg Gln Phe Phe Leu Glu Leu
        195                 200                 205
Val Lys Asp Ile Ser Asn Asp Leu Asp Leu Thr Ser Leu Ser Tyr Lys
    210                 215                 220
Ile Leu Ile Phe Val Cys Leu Met Val Asp Ala Asp Arg Cys Ser Leu
225                 230                 235                 240
Phe Leu Val Glu Gly Ala Ala Gly Lys Lys Thr Leu Val Ser Lys
                245                 250                 255
Phe Phe Asp Val His Ala Gly Thr Pro Leu Leu Pro Cys Ser Ser Thr
            260                 265                 270
Glu Asn Ser Asn Glu Val Gln Val Pro Trp Gly Lys Gly Ile Ile Gly
        275                 280                 285
Tyr Val Gly Glu His Gly Glu Thr Val Asn Ile Pro Asp Ala Tyr Gln
    290                 295                 300
Asp Arg Arg Phe Asn Asp Glu Ile Asp Lys Leu Thr Gly Tyr Lys Thr
305                 310                 315                 320
Lys Ser Leu Leu Cys Met Pro Ile Arg Ser Ser Asp Gly Glu Ile Ile
                325                 330                 335
Gly Val Ala Gln Ala Ile Asn Lys Ile Pro Glu Gly Ala Pro Phe Thr
            340                 345                 350
Glu Asp Asp Glu Lys Val Met Gln Met Tyr Leu Pro Phe Cys Gly Ile
        355                 360                 365
Ala Ile Ser Asn Ala Gln Leu Phe Ala Ala Ser Arg Lys Glu Tyr Glu
    370                 375                 380
Arg Ser Arg Ala Leu Leu Glu Val Val Asn Asp Leu Phe Glu Glu Gln
385                 390                 395                 400
Thr Asp Leu Glu Lys Ile Val Lys Lys Ile Met His Arg Ala Gln Thr
                405                 410                 415
Leu Leu Lys Cys Glu Arg Cys Ser Val Leu Leu Leu Glu Asp Ile Glu
            420                 425                 430
Ser Pro Val Val Lys Phe Thr Lys Ser Phe Glu Leu Met Ser Pro Lys
        435                 440                 445
Cys Ser Ala Asp Ala Glu Asn Ser Phe Lys Glu Ser Met Glu Lys Ser
    450                 455                 460
Ser Tyr Ser Asp Trp Leu Ile Asn Asn Ser Ile Ala Glu Leu Val Ala
465                 470                 475                 480
Ser Thr Gly Leu Pro Val Asn Ile Ser Asp Ala Tyr Gln Asp Pro Arg
                485                 490                 495
```

-continued

```
Phe Asp Ala Glu Ala Asp Gln Ile Ser Gly Phe His Ile Arg Ser Val
             500                 505                 510

Leu Cys Val Pro Ile Trp Asn Ser Asn His Gln Ile Ile Gly Val Ala
             515                 520                 525

Gln Val Leu Asn Arg Leu Asp Gly Lys Pro Phe Asp Asp Ala Asp Gln
             530                 535                 540

Arg Leu Phe Glu Ala Phe Val Ile Phe Cys Gly Leu Gly Ile Asn Asn
545                 550                 555                 560

Thr Ile Met Tyr Asp Gln Val Lys Lys Ser Trp Ala Lys Gln Ser Val
                 565                 570                 575

Ala Leu Asp Val Leu Ser Tyr His Ala Thr Cys Ser Lys Ala Glu Val
             580                 585                 590

Asp Lys Phe Lys Ala Ala Asn Ile Pro Leu Val Ser Glu Leu Ala Ile
             595                 600                 605

Asp Asp Ile His Phe Asp Asp Phe Ser Leu Asp Val Asp Ala Met Ile
         610                 615                 620

Thr Ala Ala Leu Arg Met Phe Met Glu Leu Gly Met Val Gln Lys Phe
625                 630                 635                 640

Lys Ile Asp Tyr Glu Thr Leu Cys Arg Trp Leu Leu Thr Val Arg Lys
                 645                 650                 655

Asn Tyr Arg Met Val Leu Tyr His Asn Trp Arg His Ala Phe Asn Val
             660                 665                 670

Cys Gln Leu Met Phe Ala Met Leu Thr Thr Ala Gly Phe Gln Asp Ile
         675                 680                 685

Leu Thr Glu Val Glu Ile Leu Ala Val Ile Val Gly Cys Leu Cys His
         690                 695                 700

Asp Leu Asp His Arg Gly Thr Asn Asn Ala Phe Gln Ala Lys Ser Gly
705                 710                 715                 720

Ser Ala Leu Ala Gln Leu Tyr Gly Thr Ser Ala Thr Leu Glu His His
                 725                 730                 735

His Phe Asn His Ala Val Met Ile Leu Gln Ser Glu Gly His Asn Ile
             740                 745                 750

Phe Ala Asn Leu Ser Ser Lys Glu Tyr Ser Asp Leu Met Gln Leu Leu
             755                 760                 765

Lys Gln Ser Ile Leu Ala Thr Asp Leu Thr Leu Tyr Phe Glu Arg Arg
770                 775                 780

Thr Glu Phe Phe Glu Leu Val Ser Lys Gly Glu Tyr Asp Trp Asn Ile
785                 790                 795                 800

Lys Asn His Arg Asp Ile Phe Arg Ser Met Leu Met Thr Ala Cys Asp
                 805                 810                 815

Leu Gly Ala Val Thr Lys Pro Trp Glu Ile Ser Arg Gln Val Ala Glu
             820                 825                 830

Leu Val Thr Ser Glu Phe Phe Glu Gln Gly Asp Arg Glu Arg Leu Glu
             835                 840                 845

Leu Lys Leu Thr Pro Ser Ala Ile Phe Asp Arg Asn Arg Lys Asp Glu
         850                 855                 860

Leu Pro Arg Leu Gln Leu Glu Trp Ile Asp Ser Ile Cys Met Pro Leu
865                 870                 875                 880

Tyr Gln Ala Leu Val Lys Val Asn Val Lys Leu Lys Pro Met Leu Asp
                 885                 890                 895

Ser Val Ala Thr Asn Arg Ser Lys Trp Glu Glu Leu His Gln Lys Arg
             900                 905                 910

Leu Leu Ala Ser Thr Ala Ser Ser Ser Pro Ala Ser Val Met Val
```

Ala Lys Glu Asp Arg Asn
    930

<210> SEQ ID NO 17
<211> LENGTH: 20
<212> TYPE: DNA
<213> ORGANISM: Homo sapiens

<400> SEQUENCE: 17
ttcatctccc aggtttgctc                                               20

<210> SEQ ID NO 18
<211> LENGTH: 20
<212> TYPE: DNA
<213> ORGANISM: Homo sapiens

<400> SEQUENCE: 18
cagcatcagc actgcactttt                                              20

<210> SEQ ID NO 19
<211> LENGTH: 20
<212> TYPE: DNA
<213> ORGANISM: Homo sapiens

<400> SEQUENCE: 19
ggcaggtgaa aagtccactg                                               20

<210> SEQ ID NO 20
<211> LENGTH: 20
<212> TYPE: DNA
<213> ORGANISM: Homo sapiens

<400> SEQUENCE: 20
attctttcct tgaggcagca                                               20

<210> SEQ ID NO 21
<211> LENGTH: 20
<212> TYPE: DNA
<213> ORGANISM: Homo sapiens

<400> SEQUENCE: 21
gaggtgctct ttctggatcg                                               20

<210> SEQ ID NO 22
<211> LENGTH: 20
<212> TYPE: DNA
<213> ORGANISM: Homo sapiens

<400> SEQUENCE: 22
ttgggccaca ccaataatct                                               20

<210> SEQ ID NO 23
<211> LENGTH: 34
<212> TYPE: DNA
<213> ORGANISM: Homo sapiens

<400> SEQUENCE: 23
gctagcctcg aggaaagcag ctgtctggga ccat                               34

<210> SEQ ID NO 24
<211> LENGTH: 38
<212> TYPE: DNA

```
<213> ORGANISM: Homo sapiens

<400> SEQUENCE: 24
gctagcgcgg ccgcctgcag ctgacctggc ggtttagt                          38

<210> SEQ ID NO 25
<211> LENGTH: 444
<212> TYPE: DNA
<213> ORGANISM: Homo sapiens

<400> SEQUENCE: 25
taaaaacatt ttatttctca tcatagataa aggaaaagaa agtatgtgta aagattgatt   60
gtgatttgcg aagggttcag tttgtaaaaa aaatggatca ttctagcaaa gtgtttgaca  120
aagcaccctg taaaatactt tggtgtaata aagcgaggtt cttcctgccc cccattctag  180 gcaattttg atcggaaccg aaggatgaa ctgcctgggt tgcaactgga gtggattgat    240
agcatctgca tgcctttgta tcaggtactt tgatttggga gggcctacat gttctgactg  300
aatcagaaaa ggaaaagtgt gtatttctca aaagcactca tttgaggaga catttccagg  360
gtatgcacat tgcggagagc tctggctgca gtttgtcttt cttggatttc tgactgtgcc  420
ctggctggga agagttggtt ctag                                         444
```

PDE11A MUTATIONS IN ADRENAL DISEASE

CROSS-REFERENCE TO RELATED APPLICATIONS

This patent application is a U.S. National Phase of International Patent Application No. PCT/US07/60746, filed Jan. 19, 2007, which claims the benefit of U.S. Provisional Patent Application No. 60/761,446, filed Jan. 24, 2006.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 14,294 Byte ASCII (Text) file named "703084ST25.TXT," created on May 27, 2008.

BACKGROUND OF THE INVENTION

Cushing's syndrome (CS) is a hormonal disorder caused by prolonged exposure of the body's tissues to high levels of the hormone cortisol. CS in childhood can be caused by genetic forms of bilateral adrenocortical hyperplasia (BAH). Macronodular BAR can be caused by GNAS mutations associated with either McCune-Albright syndrome (MAS) or sporadic adrenal tumors. Micronodular BAH, and its better-known pigmented variant, primary pigmented nodular adrenocortical disease (PPNAD) are caused by germline inactivating mutations of the PRKAR1A gene. Most patients with PPNAD also have Carney Complex (CNC), an autosomal dominant multiple neoplasia syndrome associated with skin lesions, cardiac myxomas, and other non-endocrine and endocrine tumors. In most patients with CNC, the disease is caused by PRKAR1A mutations.

Over the last several years, it has become apparent that there is more than one form of micronodular BAR. Recently, patients were identified with a previously uncharacterized form of micronodular BAH presenting at a young age (Gunther et al., *J. Clin. Endocrinol. Metab.*, 89, 3173-3182 (2004)). Little is known about this newly discovered form of micronodular BAR.

There remains a need for methods, compounds, and compositions that can be used to research, screen for, treat, or prevent Cushing's syndrome and its underlying causes, especially the newly discovered form of micronodular BAH presenting in young children. Such methods, compounds, and compositions are provided herein.

BRIEF SUMMARY OF THE INVENTION

The invention provides a method of screening for Cushing's syndrome or BAR in a mammal comprising (a) determining the activity or expression level of a PDE11A protein in a mammal, and (b) comparing the activity or expression level of the PDE11A protein in the mammal with a negative control, wherein decreased activity or expression of the PDE11A protein in the mammal as compared to the negative control is indicative of Cushing's syndrome or BAR. Similarly, the invention provides a method of screening for cancer or tumors in a mammal comprising (a) determining the activity or expression level of a PDE11A protein in a mammal, and (b) comparing the activity or expression level of the PDE11A protein in the mammal with a negative control, wherein decreased activity or expression of the PDE11A protein in the mammal as compared to the negative control is indicative of cancer or tumors in the mammal.

The invention provides a method of screening for Cushing's syndrome or BAH in a mammal comprising detecting a mutation in PDE11A of the mammal, wherein the presence of a mutation in PDE11A is indicative of Cushing's syndrome or BAH. Similarly, the invention provides a method of screening for cancer or tumors in a mammal comprising detecting a mutation in PDE11A of the mammal, wherein the presence of a mutation in PDE11A is indicative of cancer or tumors in a mammal.

The invention provides an isolated nucleic acid comprising one or more nucleic acid sequences selected from the group consisting of SEQ ID NOs: 1-5, as well a polypeptide encoded by the nucleic acid, and a vector and cell comprising the nucleic acid. Similarly, the invention provides an isolated nucleic acid sequence comprising SEQ ID NO: 25.

The invention provides a transgenic non-human mammal and a recombinant cell comprising a mutation of a nucleotide residue of PDE11A selected from the group consisting of (a) nucleotide residue 171 of Exon 3, (b) nucleotide residue 919 of Exon 4, (c) any one or more of nucleotide residues 1655-1657 of Exon 12, (d) nucleotide residue 2411 of Exon 19, and (e) any one or more of nucleotide residues 2758-2760 of Exon 23. Similarly, the invention provides a transgenic non-human mammal and a recombinant cell comprising a mutation of nucleotide residue 2599 of Exon 22 of PDE11A.

The invention provides a method of identifying an agent that modulates the activity of a polypeptide of the invention (e.g., a polypeptide encoded by a nucleic acid disclosed herein) comprising (a) contacting a cell that expresses the polypeptide with a test agent, and (b) comparing the activity or expression of the polypeptide in the presence of the test agent with the activity of the polypeptide in the absence of the test agent, wherein a difference in activity or expression of the polypeptide in the presence of the test agent as compared to the activity or expression of the polypeptide in the absence of the test agent is indicative that the test agent can modulate the activity of the polypeptide.

The invention provides a method of testing an agent for potential efficacy in treating Cushing's syndrome or BAH comprising (a) contacting a cell that expresses a PDE11A polypeptide with a test agent, and (b) comparing the activity or expression of the PDE11A polypeptide in the presence of the test agent with the activity or expression of the PDE11A polypeptide in the absence of the test agent, wherein a difference in the activity or expression of the PDE11A polypeptide in the presence of the test agent as compared to the activity or expression of the PDE11A polypeptide in the absence of the test agent is indicative of the test agent's potential efficacy against Cushing's syndrome or BAH.

The invention provides a method of testing an agent for potential efficacy in treating Cushing's syndrome or BAH comprising (a) administering a test agent to a transgenic non-human mammal of the invention, wherein the transgenic non-human mammal exhibits, prior to administration of the test agent, a phenotype selected from the group consisting of adrenal hyperplasia, endocrine cancer, non-endocrine cancer, malignant hypertension, immunosuppression, or any combination thereof, and (b) detecting a change in the phenotype of the transgenic non-human mammal subsequent to administration of the test agent, wherein amelioration of the phenotype subsequent to administration of the test agent is indicative of the test agent's potential effectiveness against Cushing's syndrome or BAH.

The invention provides a method of evaluating the safety of an inhibitor of PDE11A comprising (a) administering a PDE11A inhibitor to a mammal, (b) measuring subsequent to administration of the PDE11A inhibitor the level of cAMP or cGMP in a tissue of the mammal that normally expresses PDE11A, and (c) comparing the cAMP or CGMP level of the tissue with a negative control, wherein a change in the cAMP or cGMP level of the tissue as compared to the negative control is indicative that the inhibitor of PDE11A is unsafe for administration to humans.

The invention provides a method of evaluating the safety of an inhibitor of PDE11A comprising (a) administering the PDE11A inhibitor to a mammal, and (b) detecting subsequent to administration a histological change in a tissue of the mammal that normally expresses PDE11A, wherein a histological change in the tissue is indicative that the inhibitor of PDE11A is unsafe for administration to humans.

The invention also provides a method of evaluating the safety of an inhibitor of PDE11A comprising (a) administering the inhibitor of PDE11A to a mammal, and (b) detecting in the mammal subsequent to administration a symptom of Cushing's syndrome or BAH, wherein the presence of a symptom of Cushing's syndrome or BAH is indicative that the inhibitor of PDE11A is unsafe for administration to humans.

The invention further provides a nucleic acid probe comprising a nucleic acid sequence that binds to any of SEQ ID NOs: 1-5 or binds to a complementary sequence thereof, wherein the nucleic acid probe binds to any of SEQ ID NOs: 1-5 with greater affinity that to a non-mutant PDE11A sequence. Similarly, the invention provides a nucleic acid probe comprising a nucleic acid sequence that binds to SEQ ID NO: 25 or binds to a complementary sequence thereof, wherein the nucleic acid probe binds to SEQ ID NO: 25 with greater affinity that to a non-mutant PDE11A sequence.

Additionally, the invention provides a kit for detecting a mutation in PDE11A comprising one or more nucleic acids probes of the invention and any one or more of the following: (a) a reference nucleic acid sequence corresponding to the nucleic acid sequence of non-mutant PDE11A, its mRNA, or any relevant part thereof, (b) a reagent for detecting the nucleic acid, (c) a reagent for amplifying the nucleic acid, (d) instructions to use the nucleic acid to detect a mutation in PDE11A, (e) the location of a mutation of PDE11A, in electronic or other form, or (f) the nucleic acid sequence of any of SEQ ID NOs: 1-5 in electronic or other form. Similarly, the invention provides a kit for detecting a mutation in PDE11A comprising one or more nucleic acids probes of the invention and any one or more of the following: (a) a reference nucleic acid sequence corresponding to the nucleic acid sequence of non-mutant PDE11A, its mRNA, or any relevant part thereof, (b) a reagent for detecting the nucleic acid, (c) a reagent for amplifying the nucleic acid, (d) instructions to use the nucleic acid to detect a mutation in PDE11A, (e) the location of a mutation of PDE11A, in electronic or other form, or (f) the nucleic acid sequence of SEQ ID NO: 25 in electronic or other form.

The invention provides an array comprising one or more nucleic acid probes of the invention immobilized on a solid support.

DETAILED DESCRIPTION OF THE INVENTION

The phosphodiesterase 11A (PDE11A) locus, like that of other phosphodiesterases, has a complex genomic organization (Hetman et al., *Proc. Nalt. Acad. Sci. U.S.A.*, 97:12891-12895 (2000); Fawcett et al., *Proc. Natl. Acad. Sci. U.S.A.*, 97: 3702-3707 (2000); Yuasa et al., *J. Biol. Chem.*, 275: 31469-31479 (2000); Yuasa et al., *Eur. J. Biochem.*, 268: 4440-4448 (2001); and Yuasa et al., *Eur. J. Biochem.*, 268: 168-178 (2001)). PDE11A catalyzes the hydrolysis of both cAMP and cGMP (Saenz de Tejada et al., *Int. J. Impot. Res.*, 14(Suppl 4): S20 (2002); Gbekor et al., *J. Urol.*, 167(Suppl): 246 (2002); Loughney et al., *Int. J. Impot. Res.*, 17: 320-325 (2005); and D'Andrea et al. *J. Histochem. Cytochem.*, 53: 895-903 (2005)). Four splice variants of PDE11A have been discovered: PDE11A1, PDE11A2, PDE11A3, and PDE11A4. Expression of PDE11A1] appears to be ubiquitous, whereas the PDE11A2 and PDE11A3 isoforms are expressed in testis. Only PDE11A4 is expressed in the adrenal cortex. The mRNA transcripts corresponding to the four splice variants of PDE11A are collectively referred to herein as the "PDE11A mRNA transcripts" and the proteins encoded by the transcripts are collectively referred to herein as the "PDE11A proteins."

The invention provides a method of screening for Cushing's syndrome (CS) or bilateral adrenal hyperplasia (BAH) in a mammal on the basis of the activity or expression level of a PDE11A protein, or mutations in the PDE11A gene. Without wishing to be bound by any particular theory, it is believed that CS and BAH, especially the childhood forms of CS and BAH, can be caused by a genetic defect in PDE11A, particularly with respect to the expression of the PDE11A4 splice variant. It is further believed that the genetic defect reduces the activity of PDE11A, especially PDE11A4 which comprises exons 3-6 and 8-23 of PDE11A, either by downregulation of expression or by expression of a protein with reduced functionality, resulting in increased cAMP and/or cGMP levels that lead to the symptoms of CS or BAH.

According to one aspect, the method of screening for CS or BAN in a mammal comprises (a) determining the activity or expression level of a PDE11A protein in the mammal, and (b) comparing the activity or expression level of a PDE11A protein in the mammal with a negative (i.e., normal) control, wherein decreased activity or expression of the PDE11A protein in the mammal as compared to the negative control is indicative of CS or BAH. The PDE11A protein is preferably PDE11A4

The term "screen" or "screening" as used herein means to test or examine. For instance, screening encompasses detecting the presence of a symptom or a disease, or the propensity to develop such a symptom or disease (e.g., a symptom of BAH, CS, cancer, tumors, etc.). Screening also encompasses testing or examining compounds for a physical property or physiological effect, or the probability that a compound will exhibit a physiological effect. A method of screening, as used herein, can be used to research, detect, diagnose, treat, or prevent a condition such as BAH, CS, cancer, tumors, etc., or to discover or develop a compound for research or clinical use (e.g., to determine the efficacy, toxicity, or appropriate dosage levels of a compound).

The mammal can be any mammal, including a cat, dog, horse, rabbit, goat, monkey, cow, pig, or rodent, such as a rat, guinea pig, or mouse. The mammal is preferably a human. The mammal can be symptomatic or asymptomatic for CS or BAH. The mammal can be suspected of having CS or BAH or at risk for such a condition, for example, a mammal presenting with micronodular BAH at an early age (e.g., a human presenting with micronodular BAH under the age of 10 years, or even under the age of 7 years or 5 years), or a mammal with a family history of BAH or CS (e.g., a mammal with a blood relation to another mammal diagnosed with micronodular BAH or CS presenting at an early age).

The activity or expression level of the PDE11A protein in the mammal can be determined by any suitable method. Typically, the activity or expression level of the protein in the mammal is determined by assaying the activity or expression level of the protein in a biological sample obtained from the mammal. The biological sample can be any suitable sample, such as a sample of body fluid (e.g., blood, blood plasma, blood serum, serous fluid, lymph fluid, saliva, urine, etc) or tissue (e.g., especially tissue from the adrenal gland, or from an adrenal tumor). The sample is preferably a sample of the adrenal gland of the mammal. The biological sample also can be any isolated or fractioned component of the foregoing (e.g., isolated DNA, RNA, or protein from a sample of body fluid or tissue).

The activity level of a PDE11A protein can be determined by assaying or measuring the affinity of the protein for its substrate, the kinetics of the reaction of the PDE11A protein with its substrate, or the rate or degree of catalysis of the substrate. For example, the activity level of a PDE11A protein can be determined by assaying or measuring the ability (i.e., catalytic efficiency) of the protein to hydrolyze cyclic adenosine 3',5'-monophosphate (cAMP) or cyclic guanosine 3',5'-monophosphate (cGMP). The enzyme activity of a PDE11A protein also can be determined indirectly by detecting abnormal cAMP or cGMP levels in a tissue that expresses the PDE11A protein. For example, deficient PDE11A4 activity will result in elevated cAMP or cGMP levels in tissues that normally express PDE11A4, such as the adrenal glands, prostate, or testes. Specific protocols for suitable assays are known in the art.

The expression level of a PDE11A protein can be determined on the basis of mRNA or protein quantification. Specific protocols for quantifying mRNA and protein levels are known in the art (e.g., microarray analysis and Western blot). Probes and antibodies useful for such procedures can be generated from the sequences provided herein using routine techniques, some of which are discussed in connection with other aspects of the invention.

The negative (i.e., normal) control can be any suitable control or standard that reflects the activity or expression level of the PDE11A protein of interest in a mammal that contains a non-mutant PDE11A gene. Typically, the negative control will be the activity or expression level of the PDE11A protein in an appropriate mammal with a non-mutant PDE11A, such as a mammal that does not have CS or BS or any other condition associated with a mutation in PDE11A. The control also can be provided by a compilation of activity or expression levels of the PDE11A protein from a pool of such individuals (e.g., a standardized activity or expression profile of the PDE11A protein of interest).

While any decrease in the activity or expression level of the PDE11A protein relative to the negative control can be indicative of CS or BAH, it is believed, without wishing to be bound by any particular theory, that the likelihood that CS or BAH is present increases with greater deviance from the negative control. Thus, while a positive result in the screen can be indicated by a decrease in PDE11A activity or expression relative to the negative control of any amount, preferably a positive result is indicated by a decrease of at least about 10% or more (e.g., at least about 15% or more, 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or even about 100%).

In a related aspect, the method of screening for CS or BAH in a mammal comprises detecting in the mammal a mutation in PDE11A4 or the gene product of PDE11A, especially a mutation in PDE11A4 (e.g., the PDE11A4 mRNA or protein). The mammal can be any mammal as previously described, preferably a human.

A mutation in PDE11A or its gene product can be detected, for instance, by obtaining a sample from the mammal, which can be any sample as previously described that contains genetic material, and isolating and sequencing the PDE11A gene or gene product. The sequence of the PDE11A gene or gene product can then be compared to the sequence of a known normal (non-mutant) PDE11A gene or gene product, as appropriate. Normal, non-mutant PDE11A genes include any naturally occurring PDE11A gene that produces a fully-functional gene product in vivo at an expression level that is equivalent to the expression level in a normal control. A normal control is as previously defined herein.

By way of example, a normal non-mutant human PDE11A gene sequence is referenced by GenBank Accession No. ABO48423. The sequences of the mRNA and protein gene products of the PDE11A gene are referenced by GenBank Accession Nos. NM_016953 and NP_058649, respectively. The amino acid sequences of the isoforms of PDE11A include GenBank Accession Nos. BAB62714, BAB62713, and BAB52712. Nucleic acid probes suitable for isolating PDE11A or its mRNA transcripts can be designed from the nucleic acid sequences provided herein using routine techniques. Similarly, antibodies and antibody fragments suitable for isolating PDE11A proteins, especially PDE11A4, are commercially available or known in the art, or can be obtained using the polypeptides encoded by the nucleic acid sequences disclosed herein by routine techniques. Nucleic acid probes and antibodies are further discussed in connection with other aspects of the invention.

Any mutation in PDE11A or the gene product thereof (e.g., a mutation in an exon of PDE11A), especially PDE11A4, can be used as a basis for a positive result in the method of screening. Preferably, the gene mutation is a fully or partially inactivating mutation. As used herein, a mutation is fully or partially inactivating if it decreases or eliminates expression of the gene product, as determined by mRNA or protein levels, or causes the gene to express a protein that is partially or completely non-functional in any respect, preferably with respect to the ability to catalyze hydrolysis of cAMP or cGMP.

By way of illustration, several naturally occurring (i.e., non-engineered) mutations have been discovered in PDE11A that result in decreased expression levels or reduced activity levels of the PDE11A gene product, particularly PDE11A4. For example, SEQ ID NO: 1 sets forth the nucleic acid sequence of Exon 3 of a naturally occurring mutant PDE11A, wherein the thymine (T) residue normally occurring at nucleotide residue 171 of the non-mutant PDE11A has been deleted resulting in a premature stop codon (c.171delTfs41X). Similarly, SEQ ID NO: 2 provides the nucleic acid sequence of Exon 4 of a naturally occurring mutant PDE11A, wherein the cysteine (C) residue normally present at residue 919 of the non-mutant PDE11A has been substituted with a thymine (T) residue (c.919C>T/p.Arg307X) resulting in a premature stop codon. SEQ ID NO: 3 provides the nucleic acid sequence of Exon 12 of a naturally occurring mutant PDE11A, wherein the TCT residues normally present at positions 1655-1657 of the non-mutant PDE11A have been replaced with two cysteine residues (CC) resulting in a premature stop codon (c.1655-1657delTCT/insCCfs15X). SEQ ID NO: 4 provides the nucleic acid sequence of Exon 19 of a naturally occurring mutant PDE11A, wherein a guanine (G) residue normally present at position of 2411 of the non-mutant PDE11A has been substituted with adenine (A). The gene mutation translates into a substitution of arginine with histidine at amino acid residue 804 of the protein product, which is a highly conserved region of the protein (c.2411G>A/p.804Arg>His). SEQ ID NO: 5 provides the nucleic acid sequence of Exon 23 of a naturally occurring mutant PDE11A, wherein TCC residues normally present at positions 2758-2760 of the non-mutant PDE11A have been deleted, resulting in a deletion of a serine residue at position 920 of the protein product (c.2758-2760delTCC/p.Ser920del). SEQ ID NO: 25 provides the nucleic acid sequence of Exon 22 (and some surrounding intronic sequence) of a naturally occurring mutant PDE11A, wherein a cysteine (C) residue normally present at position 2599 of the non-mutant PDE11A has been substituted with guanine (G). The gene mutation translates into a substitution of arginine with glycine at amino acid residue 867 of the protein product, which is a highly conserved region of the protein (c.2599C>G/p.867Arg>Gly).

Thus, while the method of screening for CS or BAH can comprise detecting any mutation in PDE11A or its gene product, the method preferably comprises detecting one or more of the forgoing specific mutations or a different mutation in the region of PDE11A in which any of the foregoing specific mutations occur. In particular, the method preferably comprises detecting a mutation in an exon of PDE11A that is part of the PDE11A4 splice variant, preferably a mutation in one or more of Exons 3, 4, 12, 19, 22, or 23 of PDE11A. More particularly, the method can comprise detecting a mutation that comprises a substitution or deletion of a nucleotide residue of non-mutant human PDE11A selected from the group consisting of (a) nucleotide residue 171 of Exon 3, (b) nucleotide residue 919 of Exon 4, (c) any one or more of nucleotide residues 1655-1657 of Exon 12, (d) nucleotide residue 2411 of Exon 19, (e) any one or more of nucleotide residues 2758-2760 of Exon 23, and (f) nucleotide residue 2599 of Exon 22. For instance, the method can comprise detecting a nucleic acid sequence of any of SEQ ID NOs: 1-5 and 25 or a nucleic acid sequence that comprises about 85% or greater, (e.g., about 90% or greater, 95% or greater, or even about 99% or greater) sequence identity to any of SEQ ID NOs: 1-5 and 25. Methods for detecting specific mutations, such as the mutations described herein, using the nucleic acid sequences provided in SEQ ID NOs: 1-5 and 25 are known in the art and are further discussed in connection with other aspects of the invention.

In a related aspect, the invention provides an isolated nucleic acid comprising a nucleic acid sequence selected from the group consisting of SEQ ID NO: 1, SEQ ID NO: 2, SEQ ID NO: 3, SEQ ID NO: 4, SEQ ID NO: 5, SEQ ID NO: 25 or a combination thereof, as well as a polypeptide encoded by the nucleic acid. Also encompassed by the invention is a nucleic acid comprising a degenerate nucleic acid sequence of any one of SEQ ID NOs: 1-5 and 25, which encode the same protein as encoded by any one of SEQ ID NOs: 1-5 and 25, or a nucleic acid sequence that is otherwise substantially identical to any one of SEQ ID NOs: 1-5 and 25. Substantially identical sequences include any sequence that has a sequence identity to any one of SEQ ID NOs: 1-5 and 25 of 85% or more, preferably 90% or more, or even 95% or more, as determined using available algorithms (e.g., the Basic Local Alignment Search Tool (BLAST) made publicly available through the National Center for Biotechnology Information, Bethesda, Md.). Similarly, the invention encompasses a polypeptide encoded by any of the foregoing nucleic acid sequences (e.g., SEQ ID NOs: 1-5 and 25 and sequences degenerate to or substantially identical to SEQ ID NOs: 1-5 and 25), which can further comprise one or more conservative amino acid substitutions, provided that such substitutions do not obliterate the function of the polypeptide. Preferably, the number of amino acid substitutions is not greater than 15% of the total number of amino acid residues, more preferably not greater than 10% or even 5% of the amino acid residues. As used herein, the term isolated means removed from its natural environment, synthetically generated, or otherwise engineered.

The nucleic acid can be provided as part of a vector (e.g., a vector comprising the nucleic acid). Any suitable vector can be used. Suitable vectors include nucleic acid vectors, such as naked DNA and plasmids, liposomes, molecular conjugates, and viral vectors, such as retroviral vectors, parvovirus-based vectors (e.g., adenoviral-based vectors and adeno-associated virus (AAV)-based vectors), lentiviral vectors (e.g., *Herpes simplex* (HSV)-based vectors), and hybrid or chimeric viral vectors, such as an adenoviral backbone with lentiviral components (see, ergs, Zheng et al., *Nat. Biotech.,* 18(2): 176-80 (2000); International Patent Application WO 98/22143; International Patent Application WO 98/46778; and International Patent Application WO 00/17376) and an adenoviral backbone with AAV components (see, e.g., Fisher et al., *Hum. Gene Ther.,* 7: 2079-2087 (1996)). Vectors and vector construction are known in the art (see, e.g., Sambrook et al., *Molecular Cloning: A Laboratory Manual,* 3$^{rd}$ Edition, Cold Spring Harbor Laboratory Press, New York (2001); and Ausubel et al., Current Protocols in Molecular Biology, Green Publishing Associates and John Wiley & Sons, New York, N.Y. (1994)).

The vector can comprise any suitable promoter and other regulatory sequences (e.g., transcription and translation initiation and termination codons) to control the expression of the nucleic acid sequence. The promoter can be a native or nonnative promoter operably linked to the nucleic acid described above. The selection of promoters, including various constitutive and regulatable promoters, is within the skill of an ordinary artisan. Examples of regulatable promoters include inducible, repressible, and tissue-specific promoters. Specific examples include viral promoters, such as adenoviral promoters, AAV promoters, and CMV promoters. Additionally, operably linking the nucleic acid described above to a promoter is within the skill in the art.

The nucleic acid or vector can be introduced into a cell, thereby providing a recombinant cell comprising the nucleic acid, optionally in a vector. Any suitable cell (e.g., an isolated cell) can be used. Examples include host cells, such as *E. coli* (e.g., *E. coli* Tb-1, TG-2, DH5α, XL-Blue MRF' (Stratagene), SA2821, and Y1090), *Bacillus subtilis, Salmonella typhimurium, Serratia marcescens, Pseudomonas* (e.g., *P. aeruginosa), N. grassa,* insect cells (e.g., Sf9, Ea4), yeast (*S. cerevisiae*) cells, and cells derived from a mammal, including human cell lines. Specific examples of suitable eukaryotic cells include VERO, HeLa, 3T3, Chinese hamster ovary (CHO) cells, W138 BHK, COS-7, and MDCK cells. Methods of introducing vectors into isolated host cells and the culture and selection of transformed host cells in vitro are known in the art and include the use of calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, and electroporation (see, e.g., Sambrook et al., supra, Davis et al., *Basic Methods in Molecular Biology* (1986), and Neumann et al., *EMBO J.* 1: 841 (1982)). Preferably, the recombinant cell expresses the polypeptide encoded by the nucleic acid of the invention.

The recombinant cell can be an isolated cell, a cell of a cell culture, a cell of a tissue, or a cell of a host, such as a mammal or human. In this regard, the invention also provides a transgenic non-human mammal or recombinant cell that comprises a mutation in one or more exons of PDE11A selected from the group consisting of Exon 3, Exon 4, Exon 12, Exon 19, Exon 22, and Exon 23. Preferably, the mutation is an inactivating mutation, such as any one or more of the specific mutations described herein with respect to the method of screening. More particularly, the transgenic non-human mammal or recombinant cell can comprise a nucleic acid having the sequence of any of SEQ ID NOs: 1-5 and 25, optionally in the form of a vector. The transgenic non-human mammal or recombinant cell can be any suitable mammal or cell, as previously described. Preferably, the transgenic non-human mammal is a mouse or other rodent. The transgenic non-human mammal desirably exhibits adrenal hyperplasia, endocrine cancer and/or other tumor conditions, non-endocrine cancer and/or other tumor conditions, malignant hypertension, or any combination thereof.

Transgenic non-human mammals can be prepared by routine methods known in the art. The term "transgenic" is intended to encompass genetically modified mammals having a deletion or other knock-out of an endogenous gene, having an exogenous gene (e.g. a nucleic acid comprising one or more nucleic acid sequences selected from the group consisting of SEQ ID NOs: 1-5 and 25) that is stably transmitted in the host cells, and/or having an exogenous promoter operably linked to a reporter gene (e.g., lacZ). Transgenic mammals can be made through homologous recombination, where the allele locus is altered. The exogenous gene is usually from a different species than the mammal host. Where the exogenous gene is a coding sequence, it usually is operably linked to a promoter, which may be constitutive or inducible, and other regulatory sequences required for expression in the host animal. Alternatively, a nucleic acid construct is randomly integrated into the genome. Vectors for stable integration include plasmids, retroviruses and other animal viruses, YACs, and the like.

DNA constructs for homologous recombination can comprise at least a portion of the mutant of the PDE11A gene with the desired genetic modification, and can include regions of homology to the target locus. DNA constructs for random integration need not include regions of homology to mediate recombination. For various techniques for transfecting mammalian cells, see Keown et al., *Methods in Enzymology*, 185: 527-537 (1990).

The modified cells or mammals can be used for any purpose. For example, the modified cells or mammals can be used for research in order to study of the physiological effect of the PDE11A mutants or in functional studies, such as drug screening, for example, to determine the effect of a candidate drug. Transgenic cells and mammals are also useful as part of a pre-clinical program.

In this respect, the invention provides a method of identifying an agent that modulates the activity or expression of a polypeptide encoded by the nucleic acid described herein, which method comprises (a) contacting a cell that expresses the polypeptide with a test agent, and (b) comparing the activity or expression of the polypeptide in the presence of the test agent with the activity or expression of the polypeptide in the absence of the test agent, wherein a difference in activity or expression is indicative that the test agent modulates the activity or expression of the polypeptide.

The term "modulate" refers to any change or alteration in the activity or expression of any of the isoforms of PDE11A (especially the PDE11A4 isoform). Modulation may be an increase or a decrease in protein activity, a change in binding characteristics, or any other change in the biological or functional properties of any of the isoforms of PDE11A. Modulation also includes an increase or decrease in the expression of any of the PDE11A isoforms to any degree. The difference in PDE11A activity or expression that is indicative that the test agent modulates PDE11A activity or expression can be a difference of any amount, but is preferably a difference of at least about 10% or greater (e.g., about 15% or greater, about 20% or greater, about 25% or greater, about 30% or greater, about 35% or greater, about 40% or greater, about 45% or greater, about 50% or greater, about 55% or greater, about 60% or greater, about 65% or greater, about 70% or greater, about 75% or greater, about 80% or greater, about 85% or greater, about 90% or greater, about 95% or greater or about 100%). The test agent preferably increases PDE11A activity or expression.

All other aspects of the method of identifying an agent that modifies the activity of the polypeptide encoded by a nucleic acid of the invention is as described herein with respect to the other aspects of the invention.

Additionally, the invention provides a method of testing an agent for potential efficacy in treating CS or DAM. In a first aspect, the method comprises (a) administering a test agent to the transgenic non-human mammal, as described herein, wherein the transgenic non-human mammal, prior to administration of the test agent, exhibits a phenotype selected from the group consisting of adrenal hyperplasia, endocrine cancer, non-endocrine cancer, malignant hypertension, immunosuppression, or any combination thereof, and (b) detecting a change in the phenotype of the transgenic non-human mammal subsequent to administration of the test agent, wherein amelioration of the phenotype is indicative of the agent's potential effectiveness against CS or BAH. As used herein, amelioration of a phenotype or condition means a lessening of the severity of the symptoms of the phenotype or condition to any degree, such as a decrease in cancer mass, a decrease in blood pressure, etc.

In another aspect, the method of testing an agent for potential efficacy in treating CS or BAH comprises (a) contacting a cell that expresses a PDE11A polypeptide with a test agent, and (b) comparing the activity or expression of the PDE11A polypeptide in the presence of the test agent with the activity or expression of the PDE11A polypeptide in the absence of the test agent, wherein a difference in the activity or expression of the PDE11A polypeptide in the presence of the test agent as compared to the activity or expression of the PDE11A polypeptide in the absence of the test agent is indicative of the test agent's potential efficacy against CS or BAH. Preferably, the PDE11A polypeptide is PDE11A4.

All other aspects of the method of testing an agent for potential efficacy in treating CS or BAH are as described herein with respect to the other aspects of the invention.

Agents that modulate the activity or expression of a PDE11A polypeptide, such as a polypeptide encoded by a nucleic acid as described herein, or an agent that exhibits efficacy in treating CS or BAH, are useful for many purposes, such as for the research, prevention, or treatment of CS or BAH. Thus, the invention further provides a method of treating or preventing CS or BAH in a mammal, comprising administering to the mammal an agent that modulates the activity or expression of a PDE11A polypeptide, especially PDE11A4 or a polypeptide encoded by a nucleic acid described herein, whereupon CS or BAH is treated or prevented. The mammal can be any mammal as defined herein with respect to other aspects of the invention. The agent can be any suitable agent that modulates the activity or expression of PDE11A, such as an agent identified using the methods described above. The agent preferably increases PDE11A activity and can include, for instance, a nucleic acid that encodes a functional PDE11A protein, especially PDE11A4. The nucleic acid can be in the form of a vector. Suitable vectors and other components of a nucleic acid construct that could be used in this capacity are as described herein with respect to other aspects of the invention or as otherwise known in the art.

One skilled in the art will appreciate that various routes of administering the agent are available, and, although more than one route can be used for administration, a particular route can provide a more immediate and more effective reaction than another route. Suitable routes of administration of the agent can include parenteral, oral, rectal, and inhaled administration. It may also be suitable to administer the agent directly to the actual tissues, for instance, when the agent includes a nucleic acid that encodes a functional PDE11A protein, optionally in the form of a vector. Accordingly, there are a wide variety of suitable formulations of compositions that can be used in the inventive methods.

The agent described above, alone or in further combination with one or more other active agents, preferably is made into a formulation suitable for parenteral administration, and most preferably intraperitoneal administration. Such a formulation can include aqueous and nonaqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit dose or multi-dose sealed containers, such as ampules and vials, and can be stored in a freeze-dried (lyophilized) condition requiring only the addition of the sterile liquid carrier, for example, water, for injections, immediately prior to use. Extemporaneously injectable solutions and suspensions can be prepared from sterile powders, granules, and tablets, as described herein.

The dose administered to a patient, such as a mammal, particularly a human, in the context of the present invention should be sufficient to effect a prophylactic or therapeutic response as desired in the mammal over a reasonable time frame. The dose will be determined by the potency of the agent as described above, the severity of a condition being treated, as well as the body weight and age of the patient. The size of the dose also will be determined by the existence of any adverse side effects that may accompany the use of the particular agent. It is always desirable, whenever possible, to keep adverse side effects to a minimum.

The dosage can be in unit dosage form, such as a tablet or capsule. The term "unit dosage form" as used herein refers to physically discrete units suitable as unitary dosages for human and mammalian subjects, each unit containing a predetermined quantity of an agent, alone or in combination with other active agents, such as anticancer agents, calculated in an amount sufficient to produce the desired effect in association with a pharmaceutically acceptable diluent, carrier, or vehicle. The specifications for the unit dosage forms of the invention depend on the particular embodiment employed and the effect to be achieved, as well as the pharmacodynamics associated with each agent in the patient. Other aspects of the method of treating or preventing CS or BAH are as described with respect to the other aspects of the invention.

One skilled in the art can easily determine the appropriate dose, schedule, and method of administration for the exact formulation of the composition being used, in order to achieve the desired effective amount in the individual patient. One skilled in the art also can readily determine and use an appropriate indicator of the effective amount of the agent of the invention by a direct or indirect analysis of appropriate patient samples (e.g., blood and/or tissues).

The invention also provides methods to evaluate the safety of an inhibitor of PDE11A, especially an inhibitor of PDE11A4. The term "inhibitor of PDE11A" or "PDE11A inhibitor" as used herein (with respect to all aspects of the invention) refers to any compound that reduces the activity or expression of PDE11A or an isoform thereof, especially PDE11A4, by any degree. Thus, a PDE11A inhibitor can reduce the activity or expression of PDE11A or an isoform thereof by 5% or more, 10% or more, 25% or more, 35% or more, 50% or more, 75% or more, or even 90% or 95% or more. A compound is considered a "PDE11A inhibitor" regardless of whether PDE11A is the primary target of the compound. Thus, for example, a compound that primarily inhibits a different member of the PDE family, but also inhibits an isoform of PDE11A to any degree, is a PDE11A inhibitor for the purposes of this invention. Examples of agents that inhibit or partially inhibit PDE11A include tadalafil (Clalis®) and sildenafil (Viagra®), which medications are widely used for the treatment of erectile dysfunction.

The safety of an inhibitor of PDE11A can be determined on the basis of the physiological effects of PDE11A inhibition, as described herein. For example, the safety of an inhibitor of PDE11A can be evaluated by a method comprising (a) administering a PDE11A inhibitor to a mammal, (b) measuring subsequent to administration of the PDE11A inhibitor the level of cAMP or cGMP in a tissue of the mammal that normally expresses PDE11A, and (c) comparing the cAMP or cGMP level of the tissue with a negative control, wherein a change in the cAMP or cGMP level of the tissue as compared to the negative control is indicative that the inhibitor of PDE11A is unsafe for administration to humans. In a related aspect, the method of evaluating the safety of an inhibitor of PDE11A can comprise (a) administering the PDE11A inhibitor to a mammal, and (b) detecting subsequent to administration a histological change in a tissue of the mammal that normally expresses PDE11A, wherein a histological change in the tissue is indicative that the inhibitor of PDE11A is unsafe for administration to humans.

Tissues that "normally" express PDE11A are defined herein as the tissues of a mammal that, in the absence of a PDE11A inhibitor, express an isoform of PDE11A. Such tissues include, for example, tissues of the adrenal gland, testes, or prostate gland. The cAMP and cGMP levels of such tissues can be determined by methods known in the art. In this regard, the "negative control" can be as described herein with respect to other aspects of the invention, and can be provided, for example, by the cAMP or eGMP level of the tested tissue in the absence of the PDE11A inhibitor (e.g., the cAMP or cGMP level of the tissue of the same test mammal prior to administration of the PDE11A inhibitor, or a mammal of the same type as the test mammal without administration of the PDE11A inhibitor). Also, the negative control can be provided by a standard profile developed from the CAMP or cGMP levels of relevant tissues from a group of such mammals.

Any change in the cAMP or cGMP level can be indicative of an unsafe compound, such as a change of about 5% or more, 10% or more, 25% or more, 35% or more, 50% or more, 75% or more, or even 90% or 95% or more. It is believed that an increase in the cAMP and/or cGMP level is indicative of a tendency to promote CS, BAH, or tumor formation in the relevant tissue.

Histological changes can be detected by histological examination techniques that are routine in the art. By "histological change" is meant a difference in the histology of the tissue subsequent to administration as compared to the histology of the tissue prior to administration. Histological changes can be inferred from a comparison of tissues of a mammal subsequent to administration to the tissues of the same type of mammal that did not undergo administration of the PDE11A inhibitor. Histological changes include tumor formation or any other change to the cells of the tissue that indicate an abnormality, especially changes to the cells that indicate cell proliferation, malignancy, or other abnormal tendency towards growth, cancer, or tumor formation.

In a related aspect, the safety of a PDE11A inhibitor can be evaluated by a method comprising (a) administering the inhibitor of PDE11A to a mammal, and (b) detecting in the mammal subsequent to administration a symptom of Cushing's syndrome or BAH, wherein the presence of a symptom of Cushing's syndrome or BAH is indicative that the inhibitor of PDE11A is unsafe for administration to humans. Any symptom of Cushing's syndrome or BAH can be used as a basis for the evaluation, including, for example, adrenal hyperplasia, endocrine cancer, non-endocrine cancer, malignant hypertension, immunosuppression, or any combination thereof. The symptoms of Cushing's syndrome or BAR can be detected using routine techniques.

Other aspects of the method of evaluating the safety of a PDE11A inhibitor are as described with respect to the other methods and compositions of the invention.

The invention further provides isolated nucleic acids that can be used as probes or primers for detecting mutations in PDE11A, as well as kits comprising such nucleic acids and methods of using the same.

An isolated nucleic acid useful as a probe or primer comprises a nucleic acid sequence that binds to any of SEQ ID NOs: 1-5 and 25 or binds to a complementary sequence thereof, preferably under high stringency conditions (e.g. a fragment of any of SEQ ID NOs: 1-5 and 25 or complementary sequence thereof). High stringency conditions, within the meaning of the present invention are conditions that allow for mismatch of four base pairs or less, preferably three base pairs or less, two base pairs or less, or even one base pair or no mismatch. Specific conditions meeting the above requirements are known in the art or can be determined by routine techniques. High stringency conditions include, for example, low salt and/or high temperature conditions, such as provided by about 0.02-0.1 M NaCl or the equivalent, at temperatures of about 50-70° C.

Nucleic acids useful as probes should bind to any of SEQ ID NOs: 1-5 and 25 with a greater affinity than to a non-mutant PDE11A sequence, under appropriate conditions (e.g., high stringency conditions), thereby allowing the use of the probe to distinguish between the mutant and non-mutant sequences. Generally, such a probe can be designed by including the site of mutation in the probe itself. Thus, an isolated nucleic acid useful as a probe preferably comprises about 5 or more (e.g., about 7 or more, 10 or more, 15 or more, 20 or more, or even 30 or more) contiguous nucleotides of any of SEQ ID NOs: 1-5 and 25 or a nucleic acid sequence that is complementary to any of SEQ ID NOs: 1-5 and 25, wherein the isolated nucleic acid comprises the region of the sequence corresponding to the PDE11A mutation. For example, since SEQ ID NO: 1 provides the sequence of a mutant PDE11A Exon 3 comprising a deletion mutation of nucleotide residue 171, an isolated nucleic acid probe based on SEQ ID NO: 1 should include nucleotide residues 206-207 of SEQ ID NO: 1 or the appropriate nucleotides of a complementary sequence that corresponds to the mutation. The same is true with respect to SEQ ID NOs: 2-5 and 25, the corresponding PDE11A mutations of which have been described elsewhere herein. Thus, a nucleic acid probe based on SEQ ID NO: 2 should comprise the nucleotide at position 60 of SEQ ID NO: 2 or the appropriate position of a complementary sequence, which corresponds to a substitution mutation of nucleotide residue 919 of Exon 4 of PDE11A. Also, a nucleotide probe based on SEQ ID NO: 3 should comprise a nucleotide at one or more of positions 276-277 of SEQ ID NO: 3 or the appropriate position of a complementary sequence, thereby reflecting the TCT deletion that corresponds to nucleotide residues 1655-1657 of Exon 12 of PDE11A. Similarly, a nucleic acid probe based on SEQ ID NO: 4 should comprise the nucleotide at position 26 of SEQ ID NO: 4 or the appropriate position of a complementary sequence, which corresponds to a substitution mutation of nucleotide residue 2411 of Exon 19 of PDE11A. As well, a nucleotide probe based on SEQ ID NO: 5 should comprise nucleotides 209-213 of SEQ ID NO: 5, thereby reflecting a deletion of TCT at nucleotide residues 2758-2760 of Exon 23 of PDE11A. A nucleic acid probe based on SEQ ID NO: 25 should comprise the nucleotide at position 217 of SEQ ID NO: 25 or the appropriate position of a complementary sequence, which corresponds to a substitution mutation of nucleotide residue 2599 of Exon 19 of PDE11A. The probe can include one or more nucleic acid analogs, labels (e.g., a radioactive or fluorescent label), or other substituents or moieties as appropriate, provided that the base-pairing function is retained.

When the isolated nucleic acid is to be used as a primer, the nucleic acid preferably binds to PDE11A at a position flanking the site of mutation. Thus, the nucleic acid preferably comprises about 5 or more (e.g., about 7 or more, 10 or more, 15 or more, 20 or more, or even 30 or more) contiguous nucleotides of any of SEQ ID NOs: 1-5 and 25 or a nucleic acid sequence that is complementary to any of SEQ ID NOs: 1-5 and 25, wherein the nucleic acid binds to PDE11A or any of SEQ ID NOs: 1-5 and 25 at a position flanking a prospective mutation site selected from the group consisting of (i) nucleotide 171 of Exon 3, (ii) nucleotide 919 of Exon 4, (iii) nucleotides 1655-1657 of Exon 12, (iv) nucleotide 2411 of Exon 19, (v) nucleotides 2758-2760 of Exon 23, or (vi) nucleotide 2599 of Exon 22. By a position "flanking" a prospective mutation site is meant a position one or more nucleotides 5' or 3' from the prospective mutation site (e.g., 3 or more, 5 or more, or 10 or more nucleotides from the prospective mutation site, or even further from the prospective mutation site). Thus, the nucleic acid useful as a primer preferably does not comprise the prospective mutation site itself.

Specific examples of primers include nucleic acids comprising a sequence selected from the group consisting of SEQ ID NOs: 6-15. For instance, primers comprising SEQ ID NOs: 6 and/or 7 can be used to amplify a nucleic acid comprising the nucleic acid sequence of SEQ ID NO: 5; primers comprising SEQ ID NOs: 8 and/or 9 can be used to amplify a nucleic acid comprising the nucleic acid sequence of SEQ ID NO: 1; primers comprising SEQ ID NOs: 10 and/or 11 can be used to amplify a nucleic acid comprising the nucleic acid sequence consisting of SEQ ID NO: 2; primers comprising SEQ ID NOs: 12 and/or 13 can be used to amplify a nucleic acid comprising the nucleic acid sequence of SEQ ID NO: 3; and primers comprising SEQ ID NOs: 14 and/or 15 can be used to amplify a nucleic acid comprising the nucleic acid sequence of SEQ ID NO: 4.

The probes and primers can be used for any purpose, but are especially useful for detecting the PDE11A mutations described herein, which are believed to be the underlying causes of a childhood form of CS and BAH. There are many different methods of using the above described probes or primers to detect such mutations. By way of example, a method of detecting a mutation in PDE11A could comprise (a) contacting a biological sample with a polynucleotide probe, as described above, and (b) detecting a hybridization complex of the polynucleotide probe with a nucleic acid, wherein the detection of a hybridization complex indicates the presence of a mutation in PDE11A4. Alternatively, the method of detecting a mutation in PDE11A can comprise (a) contacting a biological sample with a primer as described above, (b) extending the primer to generate a copy of the nucleic acid sequence that includes the prospective mutation site, and (c) detecting a difference between the sequence of the copy and the sequence of a reference non-mutant PDE11A gene. A myriad of different techniques for detecting hybridization complexes and detecting differences between two nucleic acid sequences are known in the art, any of which can be used in conjunction with the invention. Also, conditions for the hybridization of probes and primers to the target and test sequences in the context of detecting single-nucleotide polymorphisms and disease-causing point mutations are described in the art, along with specific protocols for conducting such assays that are useful in conjunction with the invention. Furthermore, many methods of designing and using probes and primers, other than those described herein, to detect nucleic acid mutations are known (see, for example, Saiki et al., *Nature,* 324: 163-166 (1986); EP 235726; and WO 89/11548), and the description of the above specific examples is not intended to be limiting.

In a related aspect, a kit for detecting a mutation in PDE11A is provided herein comprising one or more nucleic acids that bind to one or more nucleic acid sequences of SEQ ID NOs: 1-5 and 25 (e.g., a probe or primer as described herein) and any one or more of the following: (a) a reference nucleic acid sequence corresponding to nucleic acid sequence of non-mutant PDE11A, its mRNA, or any relevant part thereof, (b) a reagent for detecting the nucleic acid, (c) a reagent for amplifying the nucleic acid, (d) instructions to use the nucleic acid to detect a mutation in PDE11A, (e) the location of a mutation of PDE11A, in electronic or other form, or (f) the nucleic acid sequence of any of SEQ ID NOs: 1-5 and 25 in electronic or other form.

Also provided herein is an array comprising one or more probes, as described herein, immobilized on a solid support. For convenience in analyzing the results, the array preferably comprises fewer than 100 different types of probes, preferably fewer than 50 different types of probes, or even fewer than 25 different types of probes (e.g., fewer than 15 or even 10 or 5 different types of probes). Methods for constructing arrays, as well as other aspects and features of suitable arrays are generally known in the art, specific examples of which are described by WO 95/11995. Arrays may be provided in the form of a multiplex chip. The array also can be part of the kit of the invention.

Other aspects of the probes, primers, kits, and arrays are as described with respect to other aspects of the invention.

The invention further provides an antibody, or an antigen binding portion thereof, that binds to a polypeptide encoded by the nucleic acids described herein. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the polypeptides of the invention. Desirably, the antibody is specific for the polypeptide, such that there is minimal cross-reaction with other peptides or proteins, such as wild-type PDE11A4 protein.

Methods of testing antibodies for the ability to bind to the polypeptides are known in the art and include any antibody-antigen binding assay, such as, for example, radioimmunoassay (RIA), ELISA, Western blot, immunoprecipitation, and competitive inhibition assays (see, e.g., Janeway et al., *Immunobiology: The Immune System in Health and Disease,* 4$^{th}$ ed., Current Biology Publications: Garland Publishing, New York, N.Y., 1999)).

Suitable methods of making antibodies are known in the art. For instance, standard hybridoma methods are described in, e.g., Köhler and Milstein, *Eur. J. Immunol.,* 5: 511-519 (1976), Harlow and Lane (eds.), *Antibodies: A Laboratory Manual,* CSSH Press (1988), and C. A. Janeway et al. (eds.), *Immunobiology,* 5$^{th}$ Ed., Garland Publishing, New York, N.Y. (2001)). Alternatively, other methods, such as EBV-hybridoma methods (Haskard and Archer, *J. Immunol. Methods,* 74(2): 361-67 (1984), and Roder et al., *Methods Enzymol.,* 121: 140-67 (1986)), and bacteriophage vector expression systems (see, e.g., Huse et al., *Science,* 246, 1275-81 (1989)) are known in the art. Furthermore, methods of producing antibodies in non-human animals are described in, e.g., U.S. Pat. Nos. 5,545,806, 5,569,825, and 5,714,352.

Phage display also can be used to generate the antibody of the invention. In this regard, phage libraries encoding antigen-binding variable (V) domains of antibodies can be generated using standard molecular biology and recombinant DNA techniques (see, e.g., Sambrook et al., supra). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.,* 235: 959-973 (1994).

The invention also provides antigen binding portions of any of the antibodies described herein. The antigen binding portion can be any portion that has at least one antigen binding site, such as Fab, F(ab')$_2$, dsFv, scFv, diabodies, and triabodies.

A single chain variable region fragment (scFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering,* 7: 697-704 (1994)).

The antibodies can be used, for instance, to detect a mutant PDE11A protein (e.g., a mutant PDE11A4 protein). For example, such a method can comprise (a) contacting a biological sample with an antibody that binds to a polypeptide encoded by a nucleic acid described herein, but does not bind to a polypeptide comprising SEQ ID NO: 16 (the amino acid sequence of wild-type PDE11A protein), and (b) detecting the binding of the antibody to a polypeptide, wherein detection of the binding of the antibody to a polypeptide is indicative of the presence of the polypeptide. The detection of the binding of the antibody to the polypeptide can be done by any suitable method, such as Western blotting, immunoassays, and immunohistochemistry techniques known in the art.

Other aspects of the antibodies and method of detecting a mutant PDE11A protein are as described with respect to other aspects of the invention.

Although the foregoing has been described in reference to Cushing's syndrome and BAH, one of ordinary skill in the art will understand that the methods to research, screen for, treat, or prevent discussed herein can be used for diseases and disorders other than Cushing's syndrome or BAM that are associated with reduced activity or expression levels of PDE11A, especially PDE11A4, including tumor formation and cancer in tissues that express PDE11A, especially PDE11A4, such as the tissues of the prostate, adrenal glands, and testis.

Thus, the invention also provides method of screening for cancer or tumors in a mammal, especially with respect to a cancer or tumors of a tissue that expresses PDE11A, comprising (a) determining the activity or expression level of a PDE11A protein in a mammal, and (b) comparing the activity or expression level of the PDE11A protein in the mammal with a negative control, wherein decreased activity or expression of the PDE11A protein in the mammal as compared to the negative control is indicative of cancer or tumors in the mammal. In a related aspect, the method of screening for cancer or tumors in a mammal comprises detecting a mutation in PDE11A of the mammal, wherein the presence of a mutation in PDE11A is indicative of cancer or tumors in a mammal. All other aspects of the method of screening for cancer or tumors in a mammal are as described with respect to the other methods and compositions of the invention.

The following examples further illustrate the invention but, of course, should not be construed as in any way limiting its scope.

EXAMPLE 1

This example demonstrates the determination of the gene involved in the new form of micronodular DAM associated with CS.

Isolation of Samples

Ten patients were identified with a variant of micronodular BAH associated with an atypical, episodic form of CS in addition to the young child previously identified in Gunther et al., *J. Clin. Endocrinol. Metalb.*, 89: 3173-3182 (2004)). The 10 patients were studied clinically and underwent bilateral adrenalectomy. Blood and tissue samples were collected from the patients as described in Gunther et al., supra. When possible, tissue was collected at surgery and processed for routine histopathology and immunohistochemistry (IHC) after being formalin-fixed and paraffin-embedded; fragments were immediately frozen at −70° C. for later use. DNA was extracted from patient and tissue samples and/or cell lines using standard methods (Qiagen, Inc.). All adrenal samples were microdissected from their surrounding normal tissues; thus, mostly abnormal tissue was used for DNA, mRNA and protein studies.

The patients' adrenocortical pathology shared an overall normal size and weight of the glands with multiple small yellow-to-dark brown nodules surrounded by a cortex with a uniform appearance. Microscopically, the normal adrenocortical zonation pattern was mildly disturbed. Intracapsular aggregates of cells and cortical excresensces in the periadrenal fat were prominent and the cortical cells appeared smaller than normal. There were occasional, variably-shaped cell aggregates, round, irregular or linear, in which the cells were larger than the remainder of the cortex. Some nodules had a pigmented cytoplasm; electron microscopy showed some larger than normal nuclei and granules of lipofuscin, lipid accumulation, giant mitochondria, and dilated smooth endoplasmic reticulum, features of a cortisol-producing adrenal hyperplasia. Synaptophysin, a marker for PPNAD, also stained the nodules.

Genotyping

Single nucleotide polymorphism (SNP) genotyping was performed using the early access Affymetrix™ (Santa Clara, Calif.) Mapping 10K array according to the manufacturer's recommendations. Statistical analysis was used to reduce the number of SNPs under consideration. Loss of heterozygosity (LOH) analysis was performed to detect possible deletions in the chromosomes, as described in Zhou et al. (*Hum. Genet.*, 115: 327-330 (2004)). A p-value was calculated for each SNP with over ~200 having p-values less than 0.05.

From this analysis, several loci were identified including, most importantly, the 2q31-35 region, which also was identified by other methods. Statistically significant LOH was found for chromosome 2 SNPs (near the location of the PDE11A gene region on 2q31.2). A SNP from within the PDE11A gene (RS959157) was listed high in its probability of association with the disease in LOH analysis and was lost in all informative tumor samples from heterozygote patients.

Fluorescent In Situ Hybridization (FISH)

To ascertain that the PDE11A gene is involved in the disease, a BAC probe that contains a large part of the 3' region of the PDE11A gene was used in FISH. Specifically, the RP11-428114 BAC, a 183,436 bp BAC containing the 3'-part of the PDE11A gene that is shared by all isoforms (A1, A2, A3, and A4) and is flanked by the centromeric D2S2173 and the telomeric D2S2757 markers, was used.

The RP11-428114 BAC was screened using primers amplifying exon 15 of the PDE11A gene. The probe mapped to chromosomal 2q31.2 region. Touch preparations on sialinized slides were prepared from frozen tumor samples that were carefully microdissected from normal tissue and kept at −20° C. until hybridization. FISH was performed using the RP11-428114 BAC and other BACs containing control loci (such as one on chromosome 6q, 2p12-16, and the 17q22-24 PRKAR1A locus), and the α-satellite probe for identification of chromosome 2 (Vysis, Inc., Downers Grove, Ill.). Probes were then labeled with digoxigenin-11-dUTP (Roche Molecular Biochemicals, Indianapolis, Ind.) by nick-translation and hybridized to the touch-preparations of the tumor samples. After hybridization, cells were counterstained with 4',6'-diamidino-2-phenylindol-dihydrochloride (DAPI). Hybridization signals were analyzed with the use of a Leica epifluorescence microscope and fluorescence images were automatically captured on a Photometrics cooled-CCD camera (Photometrics, Ltd, Tuscon, Ariz.) using IP Lab Image software (Scanalytics, Inc, Fairfax, Va.). 200 interphases with strong hybridization signals were scored. Presence of more than 25% cells with only one signal was interpreted as indicative of an allelic deletion.

The RP11-428114 BAC probe hybridized to the 2q31.2 region and showed losses in tumor cells of the affected patients.

The results indicate that the PDE11A gene region is correlated with the micronodular BAH observed in patients.

EXAMPLE 2

This example demonstrates the characterization of variants and mutants of the PDE11A gene.

Samples were collected as described in Example 1. All samples were sequenced for PRKAR1A and tumor samples were also sequenced for GNAS mutations as described in Gunther et al., supra and Bertherat et al., Canc. Res., 63: 5308-5319 (2003). Sequencing analysis of the coding regions of the PRKAR1A and the GNAS genes from peripheral blood and tumor DNA, respectively, did not show any mutations.

The genomic sequence of human PDE11A4 was used to design intronic primers to amplify the 20 exons and exon/intron junctions, as provided by Yuasa et al. (Eur. J. Biochem., 268: 168-178 (2001)). PCR was performed in 50 μl of a solution containing 10 mM Tris-HCl (pH 8.3), 50 mM KCl, 2 mM MgCl$_2$, 0.2 mM dNTP, 0.5 μmol of each primer, 50 ng genomic DNA and 2.5 units of Taq DNA polymerase. The reaction consisted of 25 cycles of denaturation at 94° C. for 30 seconds, annealing for 40 seconds and extension at 72° C. for 30 seconds. The products were gel-purified and sequenced on an ABI PRISM 3730 automated DNA sequencer (Applied Biosystems). Sequences were analyzed using Vector NTI Advance™ (Invitrogen). Amplicons with sequence changes were subject to TOPO-TA cloning (Invitrogen) and plasmids were then sequenced by standard methods. The presence of all sequence alterations was confirmed at least twice by both forward and reverse sequencing or restriction enzyme-digestion.

At least a hundred unrelated healthy control subjects were also sequenced for each sequence alteration detected in the PDE11A4 gene. The PDE11A locus was checked for major deletions and other genomic rearrangements by Southern blotting in specimens that were negative for PDE11A4 mutations. There were no major alterations detected in any samples.

Four germline mutations were identified in the heterozygote state: 3 in the cohort of 10 kindreds and a fourth in a single patient from France. Three were disrupting PDE11A4 protein expression either by leading to a stop codon (c171delTfs41X) (corresponding to SEQ ID NO: 1) and c1655-1657delTCT/insCCfs15X) (corresponding to SEQ ID NO: 3) or by creating one with a base substitution (c.919C>T/p.Arg307X) (corresponding to SEQ ID NO: 2). A fourth mutation was a single base pair substitution (c.2411G>A) (SEQ ID NO: 4) leading to an amino acid replacement (804Arg>His, R804H) in a highly conserved region of the gene. This last mutation was also identified in an unrelated, single patient with an adrenal adenoma in the background of mild bilateral hyperplasia from a cohort of 15 patients with various adrenal tumors. These patients have not necessarily presented with CS or any other obvious clinical syndrome, and their tumors, in some cases, were detected incidentally. The c.2411G>A mutation has not been seen in more than 200 chromosomes tested, and is not known as a polymorphism of the PDE11A gene in the available databases. It creates a BspH1 restriction enzyme site, and is therefore relatively easy to test for. The sequence and frequency of other sequence changes in the control population are presented in Table 1.

TABLE 1

Additional polymorphisms of the PDE11A exons and their frequency.

| Sequence change | Exon | Effect | Frequency Wt/poly | Poly/poly |
|---|---|---|---|---|
| c.1072G−3c/t | 5 | intronic | 0.122 | 0.024 |
| c.1576G+26c/t | 9 | intronic | 0.286 | 0 |
| c.1577G−3c/t* | 10 | intronic | 0.28 | 0.08 |
| c.1626A/G* | 10 | Ala542>Als>542 | 0.28 | 0.08 |
| c.1788G+27t* | 10 | large intronic rearrangement | 0.28 | 0.08 |
| c.1935G+21g/a | 11 | intronic | 0.3 | 0 |
| c.1935G+39g/a | 11 | intronic | 0.04 | 0 |
| c.2244G+54g/a | 14 | intronic | 0.17 | 0 |
| c.2423A+38g/a | 16 | intronic | 0.387 | 0.29 |
| c.2758-2760delTCC (corresponding to SEQ ID NO: 5) | 23 | Ser920del | 0.5 | 0.21 |

*these variants always were found on the same chromosome.

EXAMPLE 3

This example demonstrates that PDE11A4 is the gene responsible for the new form of micronodular BAH associated with CS.

Normal adrenal, prostate, skeletal muscle and testicular mRNA was obtained from Ambion, Inc. (Austin, Tex.) and reverse transcribed into cDNA using the 1st strand cDNA synthesis kit (Invitrogen, Inc., Palo Alto, Calif.). PCR primer sequences were designed to amplify the 5'-regions of PDE11A1, -A2, -A3 and -A4 full length cDNA using Accuprime Taq high fidelity polymerase (Invitrogen, Inc.) as detailed in Table 2.

TABLE 2

Primers for amplification of the isoforms of PDE11A.

| Isoform | Primer | Sequence (5'>3') | SEQ ID NO |
|---|---|---|---|
| A1 | Forward | TTCATCTCCCAGGTTTGCTC | 17 |
| | Reverse | CAGCATCAGCACTGCACTTT | 18 |
| A2 | Forward | GGCAGGTGAAAAGTCCACTG | 19 |
| | Reverse | ATTCTTTCCTTGAGGCAGCA | 20 |
| A3 | Forward | GAGGTGCTCTTTCTGGATCG | 21 |
| | Reverse | TTGGGCCACACCAATAATCT | 23 |
| A4 | Forward | GCTAGCCTCGAGGAAAGCAGCTGTCTGGGACCAT | 23 |
| | Reverse | GCTAGCGCGGCCGCCTGCAGCTGACCTGGCGGTTTAGT | 23 |

The PDE11A4 cDNA was amplified using specific primers containing XhoI and NotI sites (which sites are indicated by underlining in Table 2) for subcloning. For transfection and expression studies, after sequence verification, the 2.8 kb amplified PDE11A4 cDNA was digested with XhoI and NotI and cloned in the pCI expression vector (Promega US, Madison, Wis.) generating a pCI-PDE11A4 construct. An antisense construct was generated using the sense sequence, which was cloned in the reverse orientation Similarly, the cDNA from the patient CAR545.03 containing the c.2411G>A/p.804Arg>His mutation (corresponding to SEQ ID NO. 4) was amplified by PCR and subcloned into the pCI expression vector generating a pCI-PDE11A4-R804H construct.

To confirm expression, pCI-PDE11A4 sense and antisense, and pCI-PDE11A4-R804H were transfected in subconfluent HEK293 cells using tipofectamine 2000 (Invitrogen). 24 hrs post-transfection, total cell lysates were obtained from PDE11A4- and mock transfected cells and subjected to Western blot analysis.

To evaluate the effects of PDE11A4 on cAMP and cGMP levels, HEK293 cells were plated in 6-well plates and transfected with pCI-PDE11A4 sense and antisense, pCI-PDE11A4-R804H1 or pCI (mock). 48 hrs posttransfection, the cells were solubilized in 500 µl of 0.1 HCl and clarified lysates were subjected to ELISA assays for cAMP and cGMP levels. Quantitative determination of cyclic AMP (cAMP) and cyclic GMP (cGMP) levels in cell lysates from tissue samples and transfected cell lines was done employing commercially available assays; the kits were obtained from R&D systems, Inc. (Minneapolis, Minn.). Both assays were based on competitive binding, in which endogenous cAMP or cGMP levels compete with a fixed amount of alkaline phosphatase-labeled cyclic nucleotides. The assays were colorimetric and absorbance was read at 405 nm.

cAMP and cGMP levels in tissue homogenates from patients with PDE11A4 mutations were increased. Specifically, the level of cAMP in patients with PDE11A4 mutations was about 0.27 pmol/ml/µg protein as compared to about 0.12 pmol/ml/µg observed in normal patients. The level of cGMP in patients with PDE11A4 mutations was about 0.35 pmol/ml/µg protein as compared to about 0.13 pmol/ml/µg observed in normal patients.

In vitro introduction of the full length PDE11A4 cDNA in HEK293 cells decreased baseline cAMP and cGMP levels, an effect that was abolished by introduction of the full length antisense construct of the PDE11A4 open reading frame. When a construct bearing the c.2411G>A substitution (R804H) (corresponding to SEQ ID NO: 4) was introduced, cAMP levels increased, whereas cGMP levels decreased, suggesting that this substitution inhibits the activity of the enzyme for cAMP only.

These data are supportive of PDE11A4 being the gene responsible for the disease in at least a subgroup of patients with micronodular BAH. The mechanism of the disease appears to be linked to increased cAMP levels in a way similar to what happens in children with adrenocorticotropic hormone (ACTH)-independent macronodular hyperplasia in the context of MAS.

EXAMPLE 4

This example demonstrates the further characterization of variants and mutants of the PDE11A gene.

The frequency of PDE11A-inactivating sequence variants was examined in a large cohort of normal subjects between the ages of 30 and 60 years old who were enrolled in the New York Cancer Project (NYCP), a long-term prospective study that monitors the effect of cancer risk behaviors and screening practices in the New York Metropolitan area (see Mitchell et al., *J. Urban Health*, 81: 301-310 (2004)). 745 randomly selected individuals enrolled in the study were screened for the presence of three truncating mutations (c.171TdelTfs41X (SEQ ID NO: 1); c.919C>T/p.Arg307X (SEQ ID NO: 2); and c.1655_1657delTCT/insCCfs15X (SEQ ID NO: 3)) and two missense substitutions within a conservative region of the enzyme (c.2411G>A/p.804Arg>His (R804H) (SEQ ID NO: 4) and c.2599C>G/p. 867Arg>Gly (R867G)) (SEQ ID NO: 25).

The truncating mutations were found among the normal subjects: 12 carried one mutant allele each with a combined frequency of 1.6%. However, these mutations were significantly more frequent among patients with adrenal tumors as compared with the NYCP subjects (P<0.0001; odds ratio, 13.1; 95% confidence interval, 3.3-51.6). The two PDE11A missense substitutions (R804H and R867G) also were found more frequently among patients with adrenocortical tumors (12% each) compared with the normal controls in the NYCP cohort (4% and 3.6%, respectively), though the observed differences did not reach statistical significance.

When studied in vitro, the R804H and R867G missense substitutions significantly affected enzymatic function with variable increases in cAMP and/or cGMP in HeLa and HEK293 cells. In particular, when a construct bearing the c.2411G>A/p.804Arg>His (R804H) substitution was introduced into HEK293 and HeLa cells, cAMP levels increased in all cells, whereas cGMP levels decreased in HEK293 cells, but not HeLa cells. These results suggest that the substitution inhibits the activity of the enzyme for cAMP (possibly in a dominant-negative manner), but has a differential effect on cGMP levels in vitro, which may be tissue-specific or dependent on other factors, such as the PDE milieu of a given cell. The experiments with a construct bearing the R867G variant showed similar changes of the cGMP, but not cAMP levels.

This data supports the association of PDE11A with low penetrance predisposition to the development of adrenal hyperplasia and/or adenomas and possibly other tumors. For the two PDE11A missense mutations (R804H and R867G), their frequency approximates that of adrenal nodules identified incidentally or in autopsy (see Barzon et al., *Eur. J. Endocrinol.*, 149: 273-285 (2003)). Therefore, it is speculated that they may be low-penetrance alleles that occur relatively frequently in the general population.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated nucleic acid comprising SEQ ID NO: 3.
2. A vector comprising the nucleic acid of claim 1.
3. An isolated cell comprising the nucleic acid of claim 1.
4. An isolated cell comprising the vector of claim 2.

* * * * *